US010000524B2

(12) United States Patent
Verhaar et al.

(10) Patent No.: US 10,000,524 B2
(45) Date of Patent: Jun. 19, 2018

(54) SYNTHESIS OF ESTETROL VIA ESTRONE DERIVED STEROIDS

(71) Applicant: Donesta Bioscience B.V., Zeist (NL)

(72) Inventors: Mark Theodoor Verhaar, Groningen (NL); Thomas Koch, Groningen (NL); Erwin Gerardus Jacobus Warmerdam, Weert (NL)

(73) Assignee: Donesta Bioscience B.V., Zeist (NL)

( * ) Notice: Subject to any disclaimer, the term of this patent is extended or adjusted under 35 U.S.C. 154(b) by 345 days.

(21) Appl. No.: 14/578,137

(22) Filed: Dec. 19, 2014

(65) Prior Publication Data

US 2015/0105362 A1 Apr. 16, 2015

Related U.S. Application Data

(63) Continuation of application No. 10/534,079, filed as application No. PCT/NL03/00782 on Nov. 7, 2003, now abandoned.

(30) Foreign Application Priority Data

Nov. 8, 2002 (EP) .................................. 02079676

(51) Int. Cl.
*C07J 1/00* (2006.01)
*C07J 21/00* (2006.01)

(52) U.S. Cl.
CPC .............. *C07J 1/007* (2013.01); *C07J 1/0059* (2013.01); *C07J 1/0066* (2013.01); *C07J 21/00* (2013.01)

(58) Field of Classification Search
CPC ........ C07J 1/0059; C07J 1/0066; C07J 1/007; C07J 21/00
See application file for complete search history.

(56) References Cited

U.S. PATENT DOCUMENTS

| | | | |
|---|---|---|---|
| 3,138,588 A | 6/1964 | Smith | |
| 3,177,206 A | 4/1965 | Smith et al. | |
| 3,433,785 A | 3/1969 | Manson et al. | |
| 4,739,078 A | 4/1988 | Pearlman | |
| 5,340,586 A | * 8/1994 | Pike | A61K 9/1647 424/426 |

FOREIGN PATENT DOCUMENTS

| | | |
|---|---|---|
| DE | 21 29 943 A | 12/1971 |
| DE | 144266 A | 10/1980 |
| EP | 0 646 592 A | 4/1995 |
| EP | 2 077 272 | 7/2009 |
| EP | 2 077 273 | 7/2009 |
| EP | 2 077 322 | 7/2009 |
| EP | 2 077 812 | 7/2009 |
| WO | WO-02/094275 A1 | 11/2002 |
| WO | WO-02/094276 A1 | 11/2002 |
| WO | WO-02/094278 A1 | 11/2002 |
| WO | WO-02/094279 A1 | 11/2002 |
| WO | WO-03/018026 | 3/2003 |
| WO | WO-03/041718 | 5/2003 |

OTHER PUBLICATIONS

Nambara et al. Steroids, (1976), 27, p. 111-122 (disclosed by Applicants).*
Cainelli, et al. "Catalytic Hydroxylation of Olefins by Polymer-Bound Osmium Tetroxide", J. Chem. Soc., Chem, Commun. (1989), pp. 45-47.
Cantrall, et al. "The Synthesis of C-15 Beta-Substituted Estra-1.3. 5(10)-trienes, II", J. Org. Chem., Jan. 1964, vol. 29, pp. 214-217.
Chemical Land data sheet: LiAlH4 (lithium aluminum hydride). Accessed May 23, 2010.
Clive, et al. "Use of Radical Ring-Opening for Introduction of Alkyl and Substituted Alkyl Groups with Stereochemical Control: A Syntheic Application of Cyclopropylcarbinyl Radicals" J. Org. Chem. (1991) vol. 56, pp. 3801-3814.
Dionne, et al. "D-ring allyl derivatives of 17beta-and 17alpha-estradiols: Chemical synthesis and 13C NMR data" Steriods (1997) vol. 62, pp. 674-681.
Fishman, et al. "Synthesis of Epimeric 15-Hydroxyestriols, New and Potential Metabolites of Estradiol", The Journal of Organic Chemistry, Aug. 1968. vol. 33, No. 8, pp. 3133-3135.
Johnson, et al. "14-Isoestrone Methyl Ether and its Identity with Totally Synthetic Material", J. Am. Chem. Soc. (1957), vol. 79, pp. 2005-2009.
Kelly, et al. "Synthetic Steriods. Part III. The Preparation of 3beta, 15beta, 17beta-Trihydroxy-androst-5-ene and the Attempted Preparation of 3beta, 15alpha, 17beta-Trihydroxy-androst-5-ene", J. Chem. Soc. (1968), pp. 416-421.
Magnus, et al. "Applications of the Beta-Azidonation Reaction to Organic Synthesis, alpha Beta-Enones, Conjugate Addition, and γ-Lactam Annulation", J. Am. Chem. Soc. (1998), vol. 120, pp. 12486-12499.
Matsui, et al. "Synthesis of Isomeric 5alpha-Androstane-3, 15, 17beta-triols", J. Chem. Soc., Perkin Trans. I, (1976), pp. 1429-1432.
Nambara, et al. "Synthesis of Esterol Monoglucuronides", Steroids. 1976, vol. 27, pp. 111-121.
Poirier, et al. "Snythesis of 17beta-Estradiol Derivatives with N-Butyl, N-Methyl, Alkylamide Side Chain at Position 15", Tetrahedron (1991), vol. 47, No. 37, pp. 7751-7766.
Reactivity Chart 1: Protection for Hydroxyl Group: Ethers. In Greene's Protective Groups in Organic Synthesis, (1999) 3E, pp. 708-711.

(Continued)

*Primary Examiner* — Yong Chu
(74) *Attorney, Agent, or Firm* — Sunit Talapatra; Foley & Lardner LLP

(57) ABSTRACT

A process is provided for the making of estetrol starting from a 3-A-oxy-estra-1,3,5(10),15-tetraen-17-one, wherein A is an $C_1$-$C_5$ alkyl group, preferably a methyl group, or a $C_7$-$C_{12}$ benzylic group, preferably a benzyl group. This process is particularly suitable to industry.

17 Claims, No Drawings

(56) References Cited

OTHER PUBLICATIONS

Sakakibara, et al. "Syntheses of (14beta, 17alpha)-14-Hydroxy- and(14beta, 17alpha)-2,14-Dihydroxyestradiols and Their Activities", Biosci. Biotech. Biochem, (1996), vol. 60, No. 3, pp. 411-414.
Simoni, et al. "The Discovery of Estrone, Estriol, and Estradiol and the Biochemical Study of Reproduction. The Work of Edward Adelbert Doisy", J. Biol. Chem (2002), vol. 277, No. 28, e17.
Suzuki, et al. "Synthesis of 15a-hydroxyestrogen 15-N-acetylglucosaminides", Steriods, 1995, vol. 60, pp. 277-284.

* cited by examiner

SYNTHESIS OF ESTETROL VIA ESTRONE DERIVED STEROIDS

CROSS-REFERENCE TO RELATED APPLICATIONS

This application is a Continuation of U.S. application Ser. No. 10/534,079, filed as the National Phase of International Patent Application No. PCT/NL2003/000782, filed Nov. 7, 2003, published as WO 2004/041839, which claims priority to European Application No. 02079676.9, filed Nov. 8, 2002. The contents of these applications are herein incorporated by reference in their entirety.

TECHNICAL FIELD OF THE INVENTION

The present invention relates to the synthesis of estetrol [estra-1,3,5(10)-trien-3,15α,16α,17β-tetraol; CAS Nr. 15183-37-6; for convenience, this compound is referred to in this patent application as "estetrol"] via estrone derived steroids, preferably to the synthesis of estetrol which is obtained with high yield and high purity.

BACKGROUND OF THE INVENTION

Estrogenic substances are commonly used in methods of Hormone Replacement Therapy (HRT) and methods of female contraception. These estrogenic substances can be divided in natural estrogens and synthetic estrogens. Examples of natural estrogens that have found pharmaceutical application include estradiol, estrone, estriol and conjugated equine estrogens. Examples of synthetic estrogens, which offer the advantage of high oral bioavailability include ethinyl estradiol and mestranol.

Recently, estetrol has been found effective as an estrogenic substance for use in HRT, disclosure of which is given in the Applicant's co-pending application WO 02/094276. Estetrol is a biogenic estrogen that is endogeneously produced by the fetal liver during human pregnancy. Other important applications of estetrol are in the fields of contraception, therapy of auto-immune diseases, prevention and therapy of breast and colon tumors, enhancement of libido, skin care, and wound healing as described in the Applicant's co-pending applications WO 02/094276, WO 02/094279, WO 02/094278, WO 02/094275, EP 2077272.9, EP 2077273.7, WO 03/041718, WO 03/018026, EP 2077812.2, and EP 2077322.2.

The synthesis of estetrol and derivatives thereof on a laboratory scale basis is known in the art: Fishman J., Guzik H., J. Org. Chem. 33, 3133-3135 (1968); Nambara T. et al., Steroids 27, 111-121 (1976); or Suzuki E. et al., Steroids 60, 277-284 (1995).

Fishman J., Guzik H., J. Org. Chem. 33, 3133-3135 (1968) discloses a successful synthesis of estetrol from an estrone derivative (compound (III); cf. for a synthesis of compound (III) Cantrall, E. W., Littell, R., Bernstein, S. J. Org. Chem 29, 214-217 (1964)). In a first step, the carbonyl group at $C_{17}$ of compound (III) was reduced with $LiAlH_4$ to estra-1,3,5(10),15-tetraene-3,17-diol (compound VIa) that was isolated as the diacetate (compound VIb). Compound VIb was subjected to cis-hydroxylation of the double bond of ring D by using $OsO_4$ which resulted into the formation of estra-1,3,5(10)-triene-3,15α,16α,17β-tetraol-3,17-diacetate (compound Ib) that under heating with $K_2CO_3$ in methanol produces estetrol (Scheme 1).

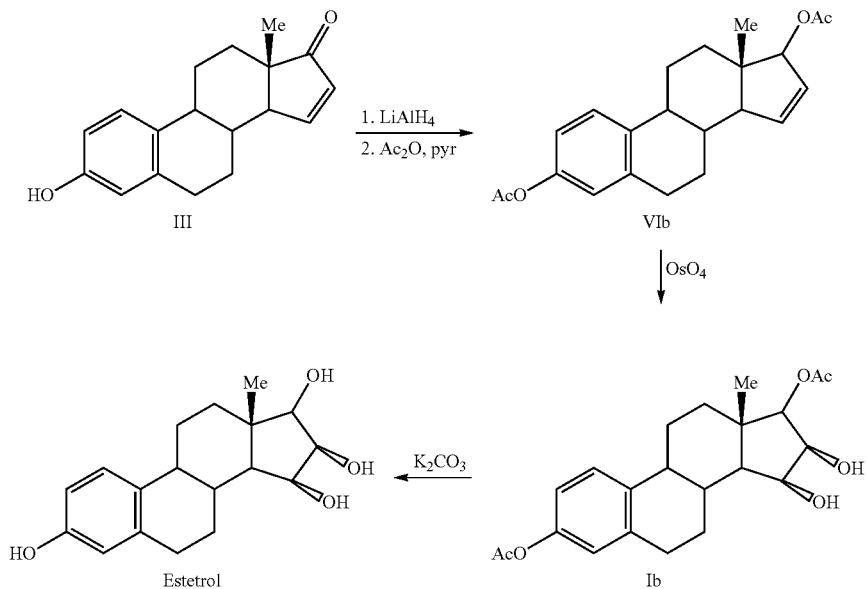

Scheme 1

The overall yield of this three step process is, starting from estrone derivative III, only about 7%. It is worth noting that the protected derivative 17,17-ethylenedioxyestra-1,3,5 (10),15-tetraene-3-ol-3-acetate (compound IV) could be cis-hydroxylated to its 15α,16α-diol derivative (compound Va), but that thereafter the dioxolane group could not be removed (p-toluene sulfonic acid in acetone at room temperature) or that the hydrolysis (aqueous sulfuric acid in warm dioxane) of the dioxolane group resulted in a mixture containing a multitude of products (Scheme 2).

Scheme 2

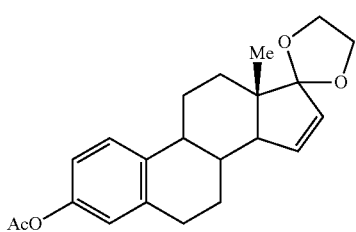

IV

Nambara T. et al., *Steroids* 27, 111-121 (1976) discloses another synthesis of estetrol wherein estrone is the starting material. The carbonyl group of estrone is first protected by treatment with ethylene glycol and pyridine hydrochloride followed by acetylation of the hydroxy group at $C_3$. The next sequence of steps involved a bromination/base catalyzed dehydrobromination resulting into the formation of 17,17-ethylenedioxyestra-1,3,5(10),15-tetraene-3-ol (compound IVa). This compound IVa was subsequently acetylated which produced 17,17-ethylenedioxyestra-1,3,5(10),15-tetraene-3-ol-3-acetate (compound IVb). In a next step, the dioxolane group of compound IVb was hydrolysed by using p-toluene sulfonic acid to compound Vb, followed subsequently by reduction of the carbonyl group at $C_{17}$ (compound Vc) and oxidation of the double bond of ring D thereby forming estra-1,3,5(10)-triene-3,15α,16α,17β-tetraol-3,17-diacetate (compound VIb). See Scheme 3.

Suzuki E. et al., *Steroids* 60, 277-284 (1995) also discloses the synthesis of estetrol by using compound Vb of Nambara T. et al. as starting material. The carbonyl group at $C_{17}$ of this compound was first reduced followed by acetylation yielding estra-1,3,5(10),15-tetraene-3,17-diol-3,17-diacetate (compound 2b). The latter was subjected to oxidation with OsO4 which provided estra-1,3,5(10)-triene-3,15α,16α,17β-tetraol-3,17-diacetate (compound 3b) in 46% yield.

Scheme 3

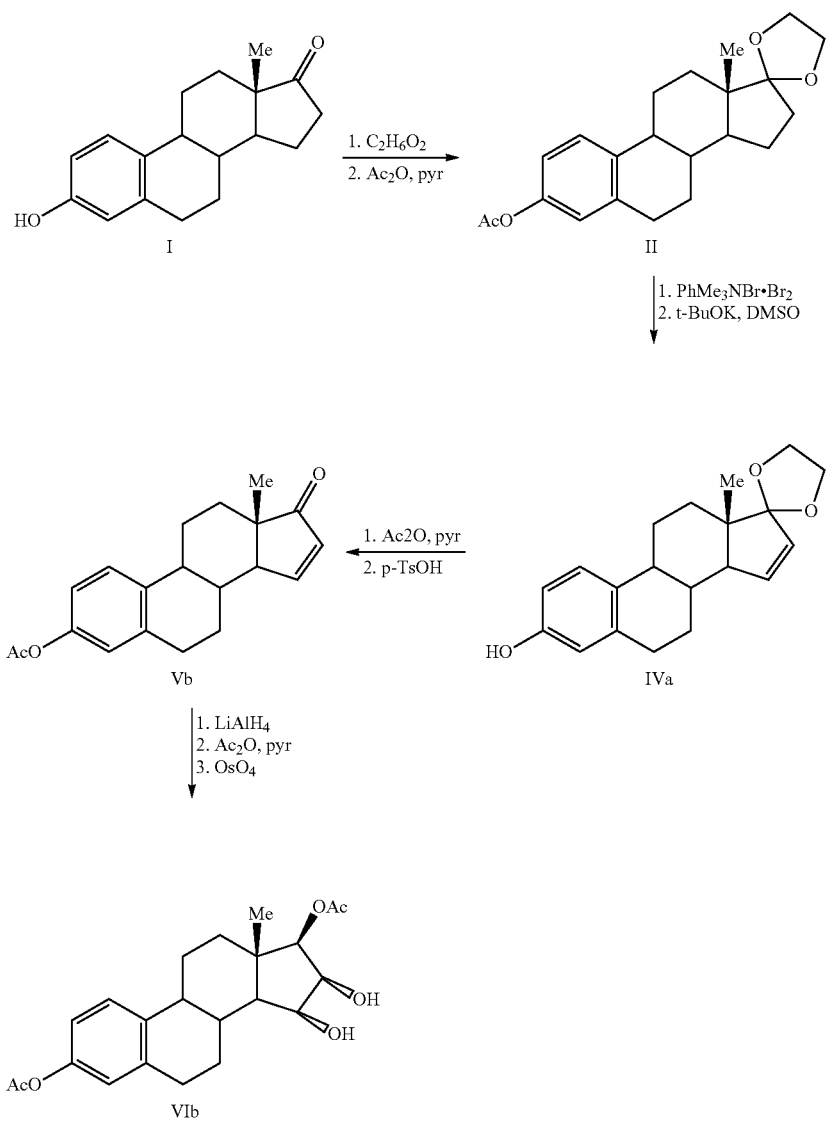

According to the Nambara T. et al. and Suzuki E. et al., the synthesis of estetrol can be performed with a yield of approximately 8%, starting from estrone.

Poirier D., et al., *Tetrahedron* 47, 7751-7766 (1991) discloses the following compounds which were prepared according to methods that have been used to prepare similar compounds:

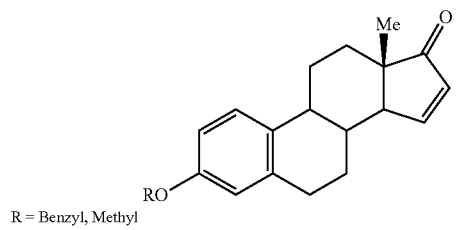

R = Benzyl, Methyl

Dionne, P. et al., *Steriods* 62, 674-681 (1997) discloses the compound shown above wherein R is either methyl or t-butyldimethylsilyl.

Magnus, P. et al., *J. Am. Chem. Soc.* 120, 12486-12499 (1998) discloses that the main methods for the synthesis of α,β-unsaturated ketones from saturated ketones are (a) halogenation followed by dehydrohalogenation, (b) utilising sulphur or selenium derivatives, (c) DDQ and (d) utilizing palladium(II) complexes.

Furthermore, it has also been found that by following the prior art methods mentioned above, estetrol of high purity was obtained only in low yield when using an acetyl group as a protecting group for the 3-hydroxy group of estra-1,3, 5(10),15-tetraen-3-ol-17-one, in particular because its sensitivity to hydrolysis and solvolysis. In particular, the lability of the acetyl group lead not only to an increased formation of byproducts during the reactions, but also during chromatography and crystallisation for purification of intermediate products when protic solvents such as methanol were used. Therefore, it is difficult to isolate purified estetrol and intermediates thereof in good yield.

Additionally, the reduction of the carbonyl group at $C_{17}$ with $LiAlH_4$ proceeds with a low selectivity since various amounts of β-estradiol (estra-1,3,5(10)-trien-3,17β-diol) are obtained as well. Obviously, the formation of such a by-product reduces the yield as well as the purity of the desired product which requires additional purification steps.

The prior art methods also employ stoichiometric amounts of $OsO_4$ in the oxidation step that is known to be a toxic and expensive compound. Consequently, the use of such a reagent is undesired in view of safety and operational costs.

Accordingly, it is an object of the present invention to provide a synthesis route for estetrol whereby high yields and high purities of estetrol are obtained.

Still accordingly, there is a need for a synthesis of estetrol wherein the production of by-products is limited. i.e. preferably less than its detection level.

It is a preferred object of the invention to provide a synthesis of estetrol wherein good yield and good purity of estetrol are provided.

By a good yield, it is meant a yield of at least 10%, preferably higher than 10%, more preferably of at least 12.5%, starting from estrone (100%).

By a good purity, it is meant a purity of at least 97%, preferably of at least 98%, more preferably of at least 99%. Preferably, single impurities are not allowed to exceed 1%. Also preferred is that β-estradiol is not allowed to exceed the detection level.

For the purpose of the present invention, determination of purity is made by HPLC-MS. The following conditions are used:

HPLC-MS is performed using a Hewlett Packard 1100 series:
Column: Discovery C18 (150×4.6 mm) Supelco
Mobile phase: Solution A:Solution B=70:30 (5 min)→(10 min)→10:90 (5 min)
Flow: 1 mL/min
UV: 280 nm
Temp: 22° C.
MS: API-ES negative
Solution A: 9.65 g $NH_4OAc$, 2250 mL $H_2O$, 150 mL MeOH, 100 mL $CH_3CN$
Solution B: 9.65 g $NH_4OAc$, 250 mL $H_2O$, 1350 mL MeOH, 900 mL $CH_3CN$ It has now been found that protecting the 3-OH group of estra-1,3,5(10),15-tetraen-3-of-17-one by an $C_1$-$C_5$ alkyl group, preferably a methyl group, or a $C_7$-$C_{12}$ benzylic group, preferably a benzyl group, fulfils such a need. Indeed, it has been found that the use of a more stable protective group such as a $C_1$-$C_5$ alkyl group, preferably a methyl group, or a $C_7$-$C_{12}$ benzylic group, preferably a benzyl group, on the 3-OH group is not cleaved at an undesired stage of the synthesis. Therefore the formation of by-products is limited and the purification of intermediates is more practical.

In this patent application the term "alkyl" includes linear, branched and cyclic alkyl groups such as methyl, ethyl, n-propyl, i-propyl, c-propyl, n-butyl, s-butyl, t-butyl, c-butyl, n-pentyl, s-pentyl, t-pentyl, c-pentyl and methylcyclobutyl. Additionally, the $C_7$-$C_{12}$ benzylic group has to be understood as a benzyl group that may be substituted with one or more substituents at the ortho, meta and/or para position of the aromatic nucleus, wherein the substituents are aliphatic groups, optionally substituted by one or more heteroatoms and/or halogen atoms that do not adversely interfere with the synthetic process. As is obvious to a skilled person in the art, the alkyl and benzylic groups are intended as a protecting group and these groups must therefore be relatively easy to add and relatively easy to remove under such conditions that do not have an adverse effect on the molecular structure of the estrone derived steroid molecules.

Because of the selected protecting groups which are used and the yield and purity obtained, it appeared that the synthesis disclosed in this patent application can be suitably transposed to an industrial scale. This represents a particular advantage in comparison to the current lab-scale syntheses which have been disclosed in the prior art and which hamper from several disadvantages as disclosed above. Indeed, a problem with industrial syntheses are the quantities of chemicals as well as the toxicity and hazardous properties thereof which are involved, thus making the prior art lab-scale methods not transposable to an industrial scale. The reason behind such impossible replication is that usually the known method either does not provide a sufficient yield, i.e. at least 10% to be considered economically feasible from an industrial point of view and/or produce by-product(s) which necessitates at least a subsequent purification step, thus raising the cost of the method.

Accordingly, it is also another preferred object of the invention to provide a method which is suitable for use in industry.

SUMMARY OF THE INVENTION

Accordingly, in one aspect of the present invention, a process is provided for the obtainment of 1,3,5(10)-estratrien-3,15α,16α,17β-tetraol which comprises the steps of:
1) 3-A-oxy-estra-1,3,5 (10), 15-tetraen-17-one wherein A is a protecting group;
2) reduction of the 17-keto group;
3) protection of the reduced carbonyl function of the 3-A-oxy-estra-1,3,5 (10), 15-tetraen-17-one;
4) oxidizing the alkene bond of the cyclopentenol moiety of the acetylated 3-A-oxy-estra-1,3,5 (10), 15-tetraen-17-ol; and
5) removing the protecting groups;
wherein the protecting group A is selected from an $C_1$-$C_5$ alkyl group, preferably a methyl group, or a $C_7$-$C_{12}$ benzylic group, preferably a benzyl group.

Hence, according to this first aspect of the invention, a process is provided for the preparation of estra-1,3,5(10)-trien-3,15α,16α,17β-tetraol (1) which comprises the steps of:
1) converting estrone (7) into 3-A-oxy-estra-1,3,5(10),15-tetraen-17-one (6), wherein A is a protecting group;
2) reduction of the 17-keto group of 3-A-oxy-estra-1,3,5 (10),15-tetraen-17-one (6) to 3-A-oxy-estra-1,3,5(10),15-tetraen-17β-ol (5);
3) protection of the 17-OH group of 3-A-oxy-estra-1,3,5 (10),15-tetraen-17β-ol (5) to 3-A-oxy-17-C-oxy-estra-1,3,5(10),15-tetraene (4), wherein C is a protecting group;
4) oxidizing the carbon-carbon double bond of ring D of 3-A-oxy-17-C-oxy-estra-1,3,5(10),15-tetraene (4) to protected estetrol (3); and
5) removing the protecting groups, wherein preferably protecting group A is removed first to form 17-OC protected estetrol (2) and subsequently protecting group C is removed to form estetrol (1);

wherein the protecting group A is selected from an $C_1$-$C_5$ alkyl group, preferably a methyl group, or a $C_7$-$C_{12}$ benzylic group, preferably a benzyl group, and the protecting group C is selected from monofunctional aliphatic hydroxyl protecting groups, said monofunctional aliphatic hydroxyl protecting groups being preferably selected from the group consisting of $C_1$-$C_5$ carboxylates wherein the alkyl group of the carboxylates is as defined above, said protecting group C being most preferably acetyl.

The process according to this first aspect of the invention is shown in Scheme 4.

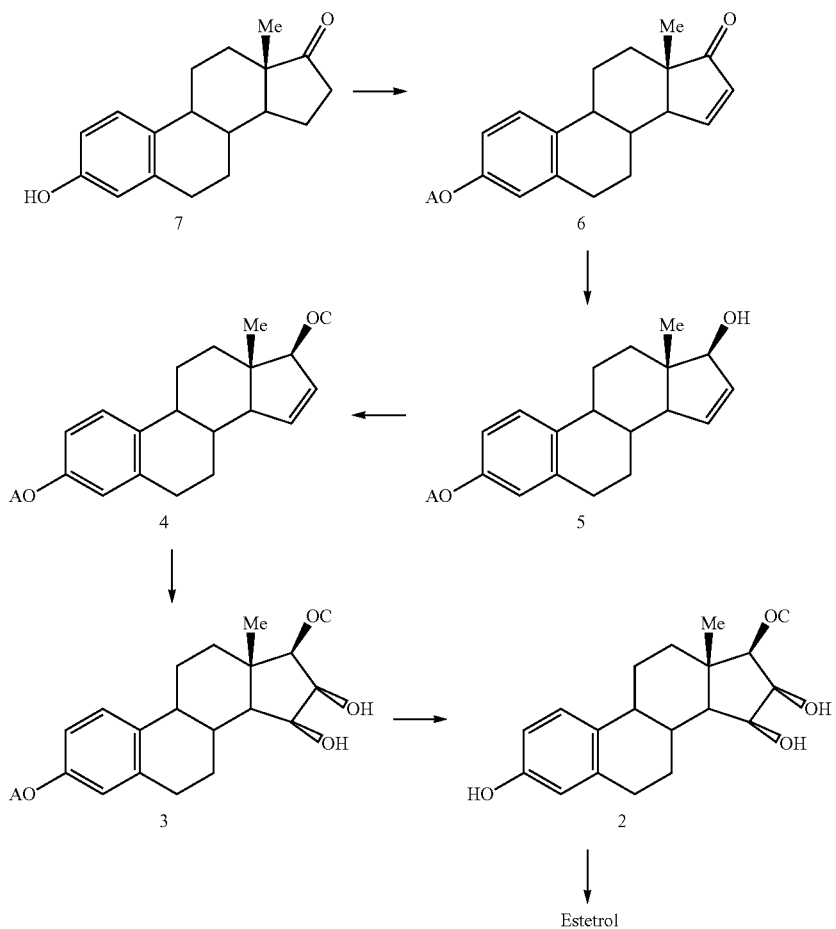

Scheme 4

In another aspect of the invention, there is provided the use of the obtained compound as estrogenic substance, preferably for cosmetic and/or therapeutic applications selected from hormone replacement therapy, contraception, therapy of autoimmune diseases, prevention and therapy of breast and colon tumors, enhancement of libido, skin care, and wound healing.

DETAILED DESCRIPTION OF THE INVENTION

According to one aspect of the invention, a process is provided for the obtainment of 1,3,5(10)-estratrien-3,15α,16α,17β-tetraol. The invention process comprises the steps of:

1) providing a 3-A-oxy-estra-1,3,5(10),15-tetraen-17-one, wherein A is a protecting group selected from an $C_1$-$C_5$ alkyl group, preferably a methyl group, or a $C_7$-$C_{12}$ benzylic group, preferably a benzyl group.

This may be achieved by methods known in the art for making such compounds such as given in *J. Am. Chem. Soc.* 79, 2005-2009 (1957), "14-Isoestrone Methyl ether and its identity with totally synthetic material" by W. S. Johnson and W. F. Johns (A is methyl); *Biosci. Biotech. Biochem.* 60, 411-414 (1996), "Synthesis of (14β,17α)-14-Hydroxy- and (14β,17α)-14-Dihydroxyestradiols and Their Activities" by M. Sakakibara and A. O. Uchida.

Still, another process of obtainment has been found effective for providing the 3-A-oxy-estra-1,3,5(10),15-tetraene-17-one (6) wherein A is a protecting group selected from a $C_1$-$C_5$ alkyl group, preferably a methyl group, or a $C_7$-$C_{12}$ benzylic group, preferably a benzyl group. This process comprises the steps of:

Step i)—protecting the phenol function of estrone by alkylation to obtain a protected estrone;
Step ii)—protecting the carbonyl function of the protected estrone obtained in step a),
Step iii)—forming an alkene bond in the $C_{15}$-$C_{16}$ position of the protected estrone obtained in step b); and
Step iv)—deprotecting the carbonyl function.

This process for the preparation of 3-A-oxy-estra-1,3,5(10),15-tetraen-17-one (6) comprises a third embodiment of the invention and comprises the following steps:

(a1) conversion of the 3-OH group of estrone (7) into a 3-AO group to form 3-A-oxy-estra-1,3,5(10)-trien-17-one (8);
(b1) conversion of the 17-keto group of 3-A-oxy-estra-1,3,5(10)-trien-17-one (8) into a protected keto group to form 3-A-oxy-17-D-estra-1,3,5(10)-triene (9);
(c1) halogenation of $C_{16}$ of 3-A-oxy-17-D-estra-1,3,5(10)-triene (9) to form 3-A-oxy-16-X-17-D-estra-1,3,5(10)-triene (10) wherein X is a halogen atom selected from the group chloride, bromide and iodide and wherein X is preferably bromide;
(d1) dehalogenation of 3-A-oxy-16-X-17-D-estra-1,3,5(10)-triene (10) to 3-A-oxy-17-D-estra-1,3,5(10),15-tetraene (11); and
(e1) deprotection of the protected keto group of 3-A-oxy-17-D-estra-1,3,5(10),15-tetraene
(11) to form 3-A-oxy-estra-1,3,5(10),15-tetraen-17-one (6), wherein A is selected from an $C_1$-$C_5$ alkyl group, preferably a methyl group, or a $C_7$-$C_{12}$ benzylic group, preferably a benzyl group, and wherein D is ethylene dioxy.

The process according to this third embodiment of the invention is depicted in Scheme 5.

Scheme 5

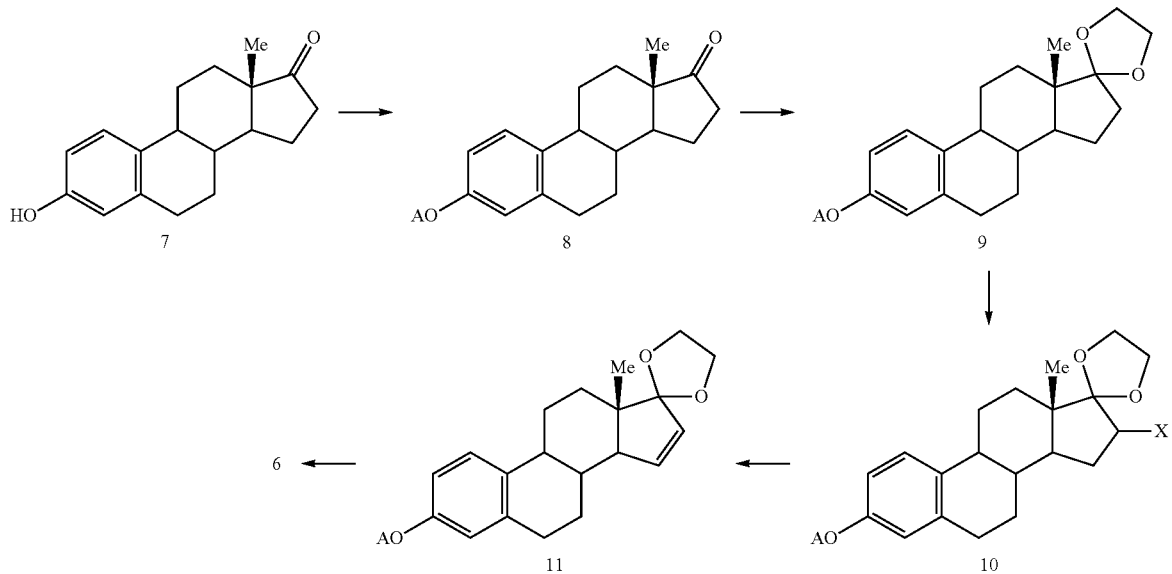

Step (a)

Estrone (7) is a product which is commercially available from Acros, Aldrich under the tradename estrone. Other suppliers of estrone are Andard-Mount Company Ltd., Diosynth B.V., Productos Quimicos Naturales S.A. de C.V.-Proquina, Schering AG,
Mistsubishi Chemical Corporation.

The protection of the 3-OH group by alkylation is typically carried out by reacting estrone with a component selected from an alkylating agent, preferably a $C_1$-$C_5$ alkyl halogenide, preferably a methyl halogenide, or a $C_7$-$C_{12}$ benzyl halogenide, preferably benzyl halogenide. Preferably, the halogen atom of the alkylating agent is bromide, chloride or iodide, most preferably bromide or iodide. According to the present invention, the most preferred alkylating agent is benzyl bromide or methyl iodide, wherein benzyl bromide is even more preferred than methyl iodide. According to the invention, however, it is possible to use a dialkyl sulphate instead of a $C_1$-$C_5$ alkyl halogenide, wherein the alkyl groups contain 1-5 carbon atoms and wherein the alkyl groups are preferably methyl (i.e. that the preferred dialkyl sulphate is dimethyl sulphate). Nevertheless, according to this embodiment of the invention, the most preferred alkylating agent is benzyl bromide.

According to this third embodiment of the present invention, it is in particular preferred to first suspend estrone (7) and potassium carbonate in a mixture of dichloromethane (DCM)/methanol. A 1:1 mixture of DCM/methanol is preferred. The alkylating agent $C_7$-$C_{12}$ benzylic halogenide, preferably benzyl bromide, is added and the resulting mixture is refluxed for a period of 8-16 hours. It is preferred to reflux the mixture for 16 hours. The reaction mixture is then cooled to Room Temperature (RT). The product is isolated by filtering off the solids. The filter cake is washed with a protic solvent, preferably methanol. The filtrate is concentrated to give a suspension which is filtered and washed with heptanes to give the product as a white solid. The product can be purified by recrystallisation from a mixture of DCM and MeOH to obtain a white crystalline solid, wherein the preferred ratio of DCM:MeOH is 1:2.

In particular, it is preferred to first suspend estrone (7) and potassium carbonate in DMF. The $C_1$-$C_5$ alkyl halogenide, preferably methyl iodide, is added with cooling, keeping the temperature between 18° and 22° C. The resulting mixture is stirred for a period of time at RT, preferably for 5 days. The reaction mixture is poured into water and stirred for 2 hours. The product is collected by filtration and washed with water. The product is dried to give a white crystalline solid.

Step b)

The protection of the 17-keto group is preferably carried out by reacting 8 with ethylene glycol using an acid catalyst such as p-toluene sulfonic acid, HCl pyridine, sulfuric acid or acetic acid and a solvent selected from dimethoxyethane, toluene, benzene, trimethyl orthoformate or triethyl orthoformate. More preferably the reaction is performed with ethylene glycol, triethyl orthoformate and p-toluenesulfonic acid.

In particular, it is preferred to suspend 8 in a mixture of triethyl orthoformate and ethylene glycol in a preferred volume ratio of 4:3, more preferably 2:1. Subsequently, p-toluenesulfonic acid is added and the reaction mixture is stirred for a period of time at 35° C. Preferably, after 1-16 hours, preferably about 3 hours, the mixture is poured into a mixture of ice/water and pyridine. After stirring for 1 h the product is collected by filtration. It is washed with water and dried to yield the product as a white solid.

Alternatively, it has also been found that steps (a) and (b) can advantageously be performed simultaneously or sequentially without the need for purification and/or isolation of the intermediate products whilst still providing an end-product with good yield and purity. This is particularly advantageous for use in industry where the reduction of the number of process step provides both an economical advantage and a simplification of the process by eliminating the need for an additional step like purification and/or isolation between the two steps.

If the process is made sequentially, the order for carrying the synthesis is preferably by having first the protection of the 3-OH group (step (a)) and then protection of the 17-keto group (step (b)). Still, it is preferred to first have step (b) and then step (a) carried out. Indeed, by use of this order, the formation of by-products has been found reduced upon industrial process.

Hence, according to a fourth embodiment of the present invention, there is provided a process for the obtainment of a 3-A-oxy-estra-1,3,5(10),15-tetraen-17-one wherein A is the protecting group selected from an $C_1$-$C_5$ alkyl group, preferably a methyl group, or a $C_7$-$C_{12}$ benzylic group, preferably a benzyl group, which process comprises the steps of:

Step ia) protecting the carbonyl function of estrone to obtain a protected estrone;

Step iia) protecting the phenol function of the protected estrone obtained in step ia) by alkylation, Step iii) forming an alkene bond in the $C_{15}$-$C_{16}$ position of the protected estrone obtained in step iia);

Step iv)—deprotecting the carbonyl function;

wherein steps ia) and iia1) are performed simultaneously or sequentially without purification and/or isolation of the obtained intermediate product.

This process for the preparation of 3-A-oxy-estra-1,3,5 (10),15-tetraen-17-one (6) comprises a fourth embodiment of the invention and comprises the following steps:

(a2) conversion of the 17-keto group of estrone (7) into a protected keto group to form 17-D-estra-1,3,5(10)-trien-3-ol (12);

(b2) conversion of the 3-OH group of 17-D-estra-1,3,5(10)-trien-3-ol (12) into a 3-AO group to form 3-A-oxy-17-D-estra-1,3,5(10)-trien-17-one (9);

(c2) halogenation of $C_{16}$ of 3-A-oxy-17-D-estra-1,3,5(10)-triene (9) to form 3-A-oxy-16-X-17-D-estra-1,3,5(10)-triene (10) wherein X is a halogen atom selected from the group chloride, bromide and iodide and wherein X is preferably bromide;

(d2) dehalogenation of 3-A-oxy-16-X-17-D-estra-1,3,5(10)-triene (10) to 3-A-oxy-17-D-estra-1,3,5(10),15-tetraene (11); and (e2) deprotection of the protected keto group of 3-A-oxy-17-D-estra-1,3,5(10),15-tetraene

(11) to form 3-A-oxy-estra-1,3,5(10),15-tetraen-17-one (6), wherein A is selected from an $C_1$-$C_5$ alkyl group, preferably a methyl group, or a $C_7$-$C_{12}$ benzylic group, preferably a benzyl group, and wherein D is ethylene dioxy.

Preferably, this is achieved by stirring a mixture of estrone (7), ethylene glycol and triethyl orthoformate to which is then added a catalytic amount of acid, preferably p-toluene sulfonic acid. The reaction temperature is then raised to between about 40° and about 60° C., preferably to about 45° C. The slurry is stirred at that same temperature until completion of the reaction, i.e. protection of the carbonyl function of estrone. The conversion is checked with HPLC. To the slurry, a solution of base, preferably sodium methoxide in methanol is added resulting in a clear yellow solution. By use of such a base, the 3-OH group is completely deprotonated which advantageously allows the use of the less reactive but more economical $C_7$-$C_{12}$ benzylic chloride, preferably benzyl chloride, in the alkylation process. The temperature is raised to 65° C. This high temperature further enables a good crystallisation of the product. Although lower temperatures such as down to 20° C. can be used, it is believed that the low temperature would incur a lower reactivity, thus longer reaction times and probably incomplete conversions. $C_7$-$C_{12}$ benzylic chloride, preferably benzyl chloride, is then added over a few minutes, such as 5 minutes, upon which the solution becomes turbid and slowly thickens into a slurry. After 1.5 hours the conversion is checked with HPLC, usually a conversion of >95% is observed, which is sufficient for further processing.

The mixture is allowed to cool to 20° C. while stirring, and then the solid product is isolated by filtration. The solid is then washed and dried.

According to the present invention, the fourth embodiment is more preferred than the third embodiment.

Step 3)

The formation of the carbon-carbon double bond in ring D is preferably carried out by steps (c2) and (d2) defined above.

The halogenation is carried out with a halogenating agent. Preferred halogenating agents are selected from bromine, phenyltrimethylammonium perbromide or pyridinium bromide perbromide. A more preferred halogenating agent for use herein is pyridinium bromide perbromide. The solvent is selected from $CHCl_3$, dioxane, dimethoxyethane, ethylene glycol or THF. The preferred solvent is THF without any co-solvent.

In particular, it is preferred to dissolve the previously obtained compound 9 in dimethoxyethane, which is subsequently added to a solution of the brominating reagent in a mixture of ethylene glycol and dimethoxyethane. The resulting mixture is stirred until completion of the reaction. Preferably after 16 hours the product is isolated. A solution of sodium thiosulfate pentahydrate in water is added to the reaction mixture. The product is extracted with an organic solvent, preferably dichloromethane. The extract is dried using sodium sulphate and the solvents are evaporated to obtain a sticky oil which can advantageously be used without further purification.

However, it is even more preferred to dissolve compound 9 in pure THF and to perform the reaction at room temperature for less than two hours, followed by removal of the THF by distillation and adding a solvent that is essential not miscible with water, preferably toluene. Water can then be removed from the product 10 by azeotropic distillation. Before the next step is performed, the toluene solution of 10 is concentrated to dryness and the solvent to be used in the next step is added.

The dehydrohalogenation reaction is carried out by using a base selected from potassium tert-butoxide, DBU (1,8-diazabicylo[5.4.0]undec-7-ene) or potassium hydroxide and is preferably potassium tert-butoxide. The solvent is selected from benzene, xylene, methanol or DMSO. The more preferred base and solvent for use in this step are respectively potassium tert-butoxide and dimethyl sulfoxide (DMSO).

In particular, it is preferred to add a suspension of the previously obtained 10 compound in DMSO to a solution of potassium tert-butoxide in DMSO. The resulting mixture is then stirred until completion of the reaction. Preferably after about 2 hours the reaction mixture is poured into a mixture of ice and water. The product is extracted with an organic solvent, preferably DCM. The extract is dried using sodium sulfate and the solvents are evaporated to obtain a sticky oil which can be used without further purification.

However, it is even more preferred to perform the dehydrohalogenation step for less than one hour and to perform the extraction with toluene at about 60° C. Furthermore, the toluene solution of compound 11 is preferably dried by azeotropic distillation before the next step is carried out.

Step 4)

Deprotection of the carbonyl function is preferably carried out by a component selected from p-toluenesulfonic acid, pyridinium p-toluenesulfonate, and pyridinium chloride, preferably p-toluenesulfonic acid monohydrate. More preferably, the deprotection is performed using p-toluenesulfonic acid monohydrate in the presence of aqueous acetone as solvent.

In particular, it is preferred to add p-toluenesulfonic acid monohydrate to a solution of the previously obtained compound in aqueous acetone, preferably with 10-20% water. The mixture is stirred until completion of the reaction. Preferably after about 3 hours, DCM and saturated aqueous sodium bicarbonate are added. After separating the layers, the aqueous layer is extracted with DCM. The combined extracts are washed with brine and concentrated to give a suspension. The product is collected by filtration and is washed with organic solvents, preferably with cold acetone and heptane. The product can be purified by recrystallization.

However, it is even more preferred to perform this deprotection step in aqueous acetone (water content about 10%) during which the product 6 crystallises from the solution. To enhance the crystallisation process, water is added after completion of the reaction which provides nice crystals that are easily collected by filtration and which eliminates the necessity of further purification, e.g. by recrystallisation.

The obtained 3-A-oxy-estra-1,3,5(10),15-tetraen-17-one (6) is advantageously used in the process for the obtainment of estetrol.

2) reduction of the 17-keto group

Reduction of the 17-keto group is preferably performed by reacting 3-A-oxy-estra-1,3,5(10),15-tetraen-17-one (6) with a reducing agent selected from the group of metal hydride compounds, said group of metal hydride compounds preferably comprising $LiAlH_4$, $AlH_3$, $NaBH_4$, $NaBH(OAc)_3$, $ZnBH_4$, and $NaBH_4/CeCl_3$. Most preferably the metal hydride compound is $NaBH_4/CeCl_3$. More preferred reducing agents for use herein are those that will provide a chemo- and stereo-selective reduction of the 17-keto group in favour of the 13 position. For that reason, the most preferred chemo- and stereo-selective reducing agent for use herein is $NaBH_4$ in combination with $CeCl_3$ hydrate, preferably the heptahydrate.

In particular, it is preferred to suspend 3-A-oxy-estra-1,3,5(10),15-tetraen-17-one (6) and $CeCl_3$ heptahydrate in a mixture of a protic solvent, preferably MeOH and THF and to stir the mixture for about 1 h at room temperature. A preferred volume ratio of MeOH to THF is 2:1 to 4:1. Then the mixture is cooled, preferably to 0°-5° C., and $NaBH_4$ is added in small portions maintaining the temperature below 8° C. After a period of time, preferably 2 hours, 1 N NaOH and DCM are added. After 30 minutes of stirring, the layers are separated and the aqueous layer is extracted with DCM. The combined organic extracts are dried with sodium sulphate and concentrated to give the product as a white solid.

However, it is even more preferred to quench the reaction mixture with an acid, preferably 2 N HCl, to remove the solvents by distillation under vacuum at about 30° to about 40° C. and to add toluene. Preferably, the temperature is then raised to about 70° C. to induce phase separation. The organic phase is then separated, washed with an aqueous solution of $Na_2CO_3$ and water. The final organic phase is dried by azeotropic distillation, cooled to about 50° C. and used for the next step.

3) Protecting the reduced carbonyl function of the 3-A-oxy-estra-1,3,5(10),15-tetraen-17-one, i.e. protection of the 17-OH group of 3-A-oxy-estra-1,3,5(10),15-tetraen-17β-ol (5) to form 3-A-oxy-17-C-oxy-estra-1,3,5(10),15-tetraene (4), wherein C is a protecting group.

The 17-OH group is protected by preferably selected by acetylation using a reagent selected from acetic anhydride or acetyl chloride. Preferably, acetic anhydride is used.

In particular, it is preferred to treat a solution of the compound in pyridine with acetic anhydride and 4-dimethylaminopyridine. The mixture is stirred for a period of time. Preferably after 2 hours at room temperature the volatiles are removed. The residue is dissolved in ethyl acetate (EtOAc)

and the resulting solution is washed with water and brine. The solution is dried using sodium sulphate and concentrated to give the crude product. Recrystallization from a mixture of organic solvents, preferably ethyl acetate, heptane and ethanol gives the product as a white solid.

However, since 4-dimethylaminopyridine is toxic and difficult to remove by distillation, it is more preferred to perform the reaction with a trialkylamine, preferably triethylamine, and an acetyl halide (about two equivalents), preferably acetyl chloride (about 1.5 equivalent) in toluene at about 25° to about 60° C., preferably about 40° to about 50° C. The work up is then performed by washing with water, aqueous acid and aqueous base. Purification of the product is then achieved by crystallisation, i.e. by removing the toluene by distillation, dissolving the crude product in ethyl acetate and heating this solution to about 70° to about 80°. To this heated solution, small portions of ethanol are added to induce crystallisation (preferred ratio of ethyl acetate to ethanol is about 1 to about 8).

4) Oxidizing the alkene bond of the cyclopentenol group of the acetylated 3-A-oxy-estra-1,3,5(10),15-tetraen-17-ol, i.e. oxidizing the carbon-carbon double bond of ring D of 3-A-oxy-17-C-oxy-estra-1,3,5(10),15-tetraene (4) to protected estetrol (3)

The oxidation of carbon-carbon double bond inn ring D is carried with an oxidising agent providing selective cis-hydroxylation of the carbon-carbon double bond. Preferably, the oxidising agent is osmium tetroxide and more preferably the oxidising agent is osmium tetroxide immobilized on PVP ($OsO_4$-PVP) that is used in a catalytic amount (cf. G. Cainelli, M. Contento, F. Manesclachi, L. Plessi, Synthesis, 45-47 (1989)) in combination with a co-oxidant selected from trimethylamine-N-oxide, N-methyl morpholine-N-oxide or hydrogen peroxide, preferably trimethylamine-N-oxide. More preferably, $OsO_4$-PVP and trimethylamine-N-oxide are used with THF as the solvent.

In particular, it is preferred to add $OsO_4$-PVP to a heated solution of the compound prepared in the previous step in THF. Preferably, the addition is performed at 50° C. followed by the addition of trimethylamine-N-oxide. Preferably, the addition of trimethylamine-N-oxide is performed portion wise during 1 hour. The mixture is stirred at this temperature for a period of time. Preferably, after 12 hours the mixture is cooled to room temperature and filtered. The volatiles are removed and the residue is dissolved in ethyl acetate and water is added. The aqueous layer is acidified and the layers are separated. The aqueous layer is extracted with ethyl acetate. The combined extracts are dried with sodium sulphate and concentrated. The resulting residue is triturated with heptanes and ethyl acetate to give the product as a white precipitate that is filtered off. The product is purified by recrystallization from a mixture of organic solvents, preferably ethyl acetate, heptane and ethanol to give the product as a white solid.

5) Removing the protecting groups A and C

Removal of the protecting groups is also an important aspect of the present invention process. Indeed, it has been found that not all protective groups can be removed without adverse effects on the obtained product. Hence, where for example a methyl group is used as the protective group for the 3-OH group, removal with pyridine.HCl has been found to lead to decomposition of the product.

Accordingly, it has been found that removal of the protecting $C_1$-$C_5$ alkyl group is preferably performed using $BBr_3$ without leading to major decomposition of the product.

Removal of the protective $C_7$-$C_{12}$ benzylic group is preferably be performed using catalytic hydrogenation conditions (Pd./$H_2$) as is well known to the person skilled in the art.

In particular, it is preferred to dissolve the protected estrone (protected estetrol (3)) in a protic solvent, preferably methanol. A catalytic amount of 10% Pd on carbon is added as a preformed suspension in methanol and the mixture is placed under an atmosphere of hydrogen, preferably 1 atmosphere. After stirring the mixture for 3 hours at room temperature it is filtered over Celite. The filtrate is concentrated to give 17-OC protected estetrol (2) as a white solid.

Removal of protecting group C is effective using a protic solvent such as methanol and a base, preferably $K_2CO_3$, to yield estetrol.

In particular, it is preferred to dissolve the compound obtained in the previous step in methanol. Potassium carbonate is added and the mixture is stirred for 2 hours at room temperature. Then the volatiles are evaporated and water and chloroform are added. The mixture is neutralized with 0.1 N HCl and the product is collected by filtration. It is then washed with water and dried to give estetrol as a white solid.

Alternatively, the order of the two deprotection steps above can be reversed. Thus, the complete deprotection can be accomplished by first deprotection of protecting group C followed by catalytic hydrogenation to remove protecting group A where A is a protective $C_7$-$C_{12}$ benzylic group. The procedures are identical to the ones described above. However, the first order of the deprotection steps that is described hereinbefore is preferred over the latter, i.e. that according to the invention it is preferred to first remove protecting group A and subsequently protective group C.

According to a most preferred embodiment of this step, the deprotection reactions, i.e. the removal of A and C, are performed in a single step if A is a protective $C_7$-$C_{12}$ benzylic group. Preferably, compound 3 is dissolved in a $C_1$-$C_3$ alkyl alcohol, preferably methanol, and subjected to hydrogenation at room temperature over night. Thereafter, the solution of compound 2 is preferably used in the subsequent step, i.e. the removal of C as described above. Work up of the reaction mixture is then preferably carried out by concentrating the solution to about 20% of its original volume and by adding an amount of water approximately equal to the volume of the concentrated solution. Thereafter, concentrated acid, preferably concentrated HCl, is added dropwise resulting in a white suspension which is filtered off, washed with water and dried.

Compounds and intermediate products that are in particular preferred according to the present invention are:
  the compound according to formula 2, wherein C is acetyl.
  compounds according to formula 3, wherein A is methyl or benzyl, preferably benzyl, and wherein C is acetyl.
  compounds according to formula 4, wherein A is methyl or benzyl, preferably benzyl, and wherein C is acetyl.
  compounds according to formula 5, wherein A is methyl or benzyl, preferably benzyl.
  compounds according to formula 8, wherein A is methyl or benzyl.
  compounds according to formula 9, wherein A is methyl or benzyl, preferably benzyl, and D is ethylene dioxy.
  compounds according to formula 10, wherein A is methyl or benzyl, preferably benzyl, D is ethylene dioxy and X is bromo.
  compounds according to formula 11, wherein A is methyl or benzyl, preferably benzyl, and D is ethylene dioxy.

Applications

In another aspect of the present invention is provided the use of the product as obtainable by the invention process for the manufacture of a pharmaceutical composition, preferably for use in a method selected from a method of hormone replacement therapy, a method of treating vaginal dryness, a method of contraception, a method of enhancing libido, a method of treating skin, a method of promoting wound healing, and a method of treating or preventing a disorder selected from the group consisting of autoimmune diseases, breast tumours and colorectal tumours.

In another aspect of the present invention is provided the cosmetic/aesthetic use of the product as obtainable by the invention process for treating skin.

EXAMPLES

The following are non-limited synthesis examples for the synthesis of estetrol according to the invention:

The following methods and materials for determination were used:

1H NMR spectra were recorded on a Varian 200 MHz apparatus in CD3OD.

HPLC-MS was performed using a Hewlett Packard 1100 series:

Column: Discovery C18 (150×4.6 mm) Supelco
Mobile phase: Solution A:Solution B=70:30 (5 min)→(10 min)→10:90 (5 min)
Flow: 1 mL/min
UV: 280 nm
Temp: 22° C.
MS: API-ES negative
Solution A: 9.65 g NH4OAc, 2250 mL H2O, 150 mL MeOH, 100 mL CH3CN
Solution B: 9.65 g NH4OAc, 250 mL H2O, 1350 mL MeOH, 900 mL CH3CN DSC was measured using a Mettler Toledo DSC822 apparatus.

Example 1
3-Benzyloxy-estra-1,3,5(10)-trien-17-one
(compound 6, A=benzyl)

To a suspension of estrone (7; 100 g, 0.370 mol) and $K_2CO_3$ (160 g, 1.16 mol) in DCM/MeOH (800 mL, 1:1 v/v ratio) at room temperature was added benzyl bromide (132 mL, 1.10 mol) in one portion. The resulting mixture was refluxed for 16 h (50% conversion after 4 h according to TLC). The reaction mixture was cooled to RT and solids were filtered off. The filter-cake was washed with MeOH. The solution was concentrated (to a total volume of ca. 300 mL). The precipitate that had formed was collected by filtration and washed with heptanes to give a white solid. The filtrate was concentrated further (to a total volume of 100 mL) and triturated with heptane. The resulting precipitate was filtered off and combined with the first batch of product. The product (153 g, max 0.370 mol) still contained traces off benzyl bromide but was used without further purification. The product can be purified by recrystallization from DCM/MeOH (1/2). TLC: $R_f$=0.5 (heptanes/ethyl acetate=4/1); HPLC-MS: 91%; $^1$H-NMR (200 MHz, CDCl$_3$) δ 7.60-7.24 (m, 5H), 7.49 (d, 1H, J=8.4 Hz), 6.87 (dd, 1H, $J_1$=2.6 Hz, $J_2$=8.4 Hz), 6.82 (d, 1H, J=2.4 Hz), 5.12 (s, 2H), 3.05-2.90 (m, 2H), 2.66-2.01 (m, 5H), 1.77-1.47 (m, 8H), 0.99 (s, 3H) ppm.

Example 2 17,17-Ethylenedioxy-3-benzyloxy estra-1,3,5(10)-trien-17-one (compound 4; A=benzyl, C=ethylene dioxy)

3-Benzyl-estrone (compound 6, A=benzyl; 153 g (crude), max. 0.370 mol) was suspended in a mixture of triethyl orthoformate (320 mL) and ethylene glycol (160 mL). p-TsOH monohydrate (5 g, 26.3 mmol) was added and the resulting pinkish suspension was stirred for 3 h at 35° C. (TLC indicated complete conversion after 1.5 h). The mixture was cooled to RT, poured into a mixture of ice-water (2 L) and pyridine (40 mL). The resulting precipitate was collected by filtration and washed with water (150 ml). The remaining white solid was dried azeotropically by stripping with toluene (2×200 mL) to afford the product (153 g, max. 0.370 mmol) as white crystalline material. TLC: $R_f$=0.3 (heptanes/ethyl acetate=9/1); $^1$H-NMR (200 MHz, CDCl$_3$) δ 7.60-7.24 (m, 5H), 7.29 (d, 1H, J=8.4 Hz), 6.86 (dd, 1H, $J_1$=2.6 Hz, $J_2$=8.4 Hz), 6.80 (d, 1H, J=2.4 Hz), 5.11 (s, 2H), 4.03 (m, 4H), 3.05-2.90 (m, 2H), 2.46-1.28 (m, 13H), 0.96 (s, 3H) ppm.

Example 3 17,17-Ethylenedioxy-3-benzyloxy estra-1,3,5(10)-trien-17-one (compound 4; A=benzyl, C=ethylene dioxy)

A reaction flask equipped with mechanical stirrer, thermometer, nitrogen purge, condenser and dropping funnel was used for the process. The flask was charged with 27 g (100 mmol) of estrone, 50 ml (55 g, 9 equivalents) of glycol and 24 g of triethylorthoformate. The resulting mixture was stirred. 0.5 g of toluenesulfonic acid was added and the reaction temperature was raised to 45° C. At about 35-40° C. an exothermic was observed. The slurry is stirred for 1 hour at 45° C. The conversion is checked with LC. Usually after 1 hour almost complete conversion is observed. To the slurry a solution of sodium methoxide in methanol (30% wt.; 1.1 equivalents) is added from the dropping funnel resulting in a clear yellow solution. The temperature is raised to 65° C. and 15 g of benzyl chloride is added over 5 minutes. Within a few minutes the solution becomes turbid and slowly thickens into a slurry. After 1.5 hours the conversion is checked with LC, usually a conversion of >95% is observed, which is sufficient for further processing.

The mixture is allowed to cool to 20° C. while stirring, and then the solid product is isolated by filtration. The solid is washed with methanol (2*30 ml) and dried under atmospheric conditions.

An amount of 33-34 g of product is obtained with an organic purity of >97%.

Example 4 16-Bromo-17,17-ethylenedioxy-3-benzyloxy-estra-1,3,5(10)-triene-17-one (compound 10, X=Br, A=benzyl, B=ethylene dioxy)

Pyridinium bromide perbromide (120 g, 375 mmol, 1.44 equiv) was dissolved in a mixture of ethylene glycol (120 mL) and ethylene glycol dimethyl ether (200 mL). 3-Benzyl-estrone ethylene glycol acetal (compound 4; A=benzyl, C=ethylenedioxy; 153 g (crude), max. 0.370 mol) was dissolved in ethylene glycol dimethyl ether (400 mL) and subsequently added to the brominating reagent within 5 minutes. The mixture became yellow immediately and was stirred for 16 h at RT (TLC showed the reaction to be converted to 50% after 2 h). A solution of $Na_2S_2O_3.5H_2O$ (205 g, 0.83 mol) in water (700 mL) was added to the reaction mixture. DCM (1 L) was added and the layers were separated. The aqueous layer was extracted with DCM (2×200 mL). The combined organic layers were washed with water (300 mL) and brine (300 mL), dried ($Na_2SO_4$) and concentrated in vacuo to yield the brominated product (180 g, max. 0.370 mol) as a yellow solid which was used without further purification for the next step. TLC: $R_f$=0.25 (heptanes/ethyl acetate=9:1); HPLC-MS: 2 diasteromers (together 85%) minor byproducts present; $^1$H-NMR (200 MHz, $CDCl_3$) δ 7.60-7.20 (m, 5H), 7.27 (d, 1H, J=8.4 Hz), 6.85 (dd, 1H, $J_1$=2.6 Hz, $J_2$=8.6 Hz), 6.80 (d, 1H, J=2.4 Hz), 5.10 (s, 2H), 4.63 (m, 1H), 4.08 (m, 4H), 2.93 (m, 2H), 2.41-1.38 (m, 11H), 0.98 (s, 3H) ppm.

Example 5 17,17-Ethylenedioxy-3-benzyloxy estra-1,3,5(10),15-tetraene (compound 11; A=benzyl, B=ethylene dioxy)

Potassium tert-butoxide (180 g, 1.6 mol) was dissolved in DMSO (600 mL) and a suspension of 16-Bromo-17,17-ethylenedioxy-3-benzyloxy-estra-1,3,5(10)-triene-17-one (compound 10, X=Br, A=benzyl, B=ethylenedioxy; 180 g (crude), max. 0.370 mol) in DMSO (600 mL) was added at RT within 5 min. The temperature rose to 45° C. during the addition. The colour of the reaction mixture immediately changed to dark brown. The reaction mixture was stirred for 2 h during which the temperature fell to 25° C. It was poured into ice/water (2 L) and extracted with DCM (2×1 L, 2×300 mL). The organic layers were combined, washed with water (300 mL) and brine (300 mL) and dried with $Na_2SO_4$. The solution was concentrated in vacuo to give the crude product (147 g, max. 0.370 mmol) as a brown oil which was used without further purification for the next step. TLC: $R_f$=0.35 (heptanes/ethyl acetate=9/1); $^1$H-NMR (200 MHz, $CDCl_3$) δ 7.60-7.44 (m, 5H), 7.27 (d, 1H, J=8.4 Hz), 6.86 (dd, 1H, $J_1$=2.6 Hz, $J_2$=8.4 Hz), 6.80 (d, 1H, J=2.4 Hz), 6.33 (dd, 1H, $J_1$=1.6 Hz, $J_2$=7.4 Hz), 5.82 (dd, 1H, $J_1$=3.4 Hz, $J_2$=6.0 Hz), 5.10 (s, 2H), 4.03 (m, 4H), 2.95 (m, 2H), 2.56-1.40 (m, 9H), 1.04 (s, 3H) ppm.

Example 6 3-Benzyloxy-estra-1,3,5 (10),15-tetraen-17-one (compound 6; A=benzyl)

To a solution of 17,17-Ethylenedioxy-3-benzyloxy estra-1,3,5(10),15-tetraene (compound 11; A=benzyl, B=ethylenedioxy; 147 g, max 0.370 mol) in acetone (0.9 L) and water (100 mL) at RT was added p-TsOH monohydrate (4.8 g, 25 mmol). The mixture was stirred for 3 h at RT (According to TLC the reaction was complete after 1 h and a precipitate had formed). DCM (1.2 L) and saturated aqueous $NaHCO_3$ solution (300 mL) were added. The mixture was stirred vigorously. The layers were separated and the aqueous layer was extracted with DCM (300 mL). The combined organic layers were washed with brine (300 mL) and concentrated until precipitation started (volume of appr. 300 mL, T=50° C.). The precipitate was filtered off, washed with cold acetone and hexanes to afford the product as an off-white solid which was purified by recrystallization from acetone to give a white solid (58 g, 0.162 mol, 44% over 5 steps). (purity according to HPLC-MS: 94%). The remaining mother-liquor still contained 40% of product according to HPLC-MS. TLC: $R_f$=0.3 (heptanes/ethyl acetate=4:1); DSC: Mp. 161.9° C. (purity 91.7%); $^1$H-NMR (200 MHz, $CDCl_3$) δ 7.70 (dd, 1H, $J_1$=1.6 Hz, $J_2$=6.0 Hz), 7.60-7.40 (m, 5H), 7.26 (d, 1H, J=8.8 Hz), 6.86 (dd, 1H, $J_1$=2.6 Hz, $J_2$=8.8 Hz), 6.84 (d, 1H, J=2.4 Hz), 6.17 (dd, 1H, $J_1$=3.8 Hz, $J_2$=6.6 Hz), 5.12 (s, 2H), 3.01 (m, 2H), 2.62-1.64 (m, 9H), 1.18 (s, 3H) ppm.

Example 7 3-Benzyloxy-estra-1,3,5 (10),15-tetraen-17-ol (compound 5; A=benzyl)

To a solution of 3-benzyl-dehydroestrone (compound 6; A=benzyl; 58 g, 162 mmol) in a mixture of MeOH (900 mL) and THF (200 mL) at room temperature was added $CeCl_3$ heptahydrate (66.4 g, 178 mmol). After stirring for 1 h the mixture was cooled to 0-5° C. using an ice/water bath. Then $NaBH_4$ (12.2 g, 324 mmol) was added in small portions maintaining a temperature below 8° C. After stirring for 2 h at 0-5° C. (TLC showed the reaction to be complete) 1 N NaOH (300 mL) and DCM (1 L) were added and the mixture was stirred for ½ h at room temperature. The layers were separated and the aqueous layer was extracted with DCM (200 mL). The organic layers were combined, dried ($Na_2SO_4$) and concentrated in vacuo to give an off-white solid (55.0 g, 152.8 mmol, 94%) TLC: $R_f$=0.25 (heptanes/ethyl acetate=4:1); HPLC-MS: 93% β-isomer, 2% α-isomer; DSC: Mp. 149.7° C., purity 96.6%; $^1$H-NMR (200 MHz, $CDCl_3$) δ 7.48 (m, 5H), 7.27 (d, 1H, J=8.4 Hz), 6.85 (dd, 1H, $J_1$=2.8 Hz, $J_2$=8.6 Hz), 6.81 (d, 1H, J=2.4 Hz), 6.10 (d, 1H, J=5.8 Hz), 5.79 (dd, 1H, $J_1$=1.8 Hz, $J_2$=3.4 Hz), 5.11 (s, 2H), 4.48 (d, 1H, J=7.6), 2.96 (m, 2H), 2.46-1.64 (m, 9H), 0.93 (s, 3H) ppm.

Example 8 17-Acetyloxy-3-benzyloxy-estra-1,3,5 (10),15-tetraene (compound 4; A=benzyl, C=acetyl)

A solution of 3-Benzyloxy-estra-1,3,5 (10),15-tetraen-17-ol (compound 5; A=benzyl; 55.0 g, max. 153 mmol) in pyridine (400 mL) was treated with $Ac_2O$ (50 mL, 0.53 mol) and 4-dimethylaminopyridine (1.5 g, 12.3 mmol). The mixture was stirred for 2 h at room temperature (TLC showed the reaction to be complete). It was concentrated in vacuo. The residue was dissolved in EtOAc (400 mL), washed with water (200 mL) and brine (150 mL), dried ($Na_2SO_4$) and concentrated in vacuo to yield a yellow solid (54.0 g, 49.8 mmol, 88%). The product was purified by recrystallization from heptanes/EtOAc/EtOH (1:0.5:1) to afford a white solid (45.0 g, 112 mmol, 73%) TLC: $R_f$=0.6 (heptanes/ethyl acetate=4/1); HPLC-MS: 98% β-isomer, 1% a-isomer, 1.3% B-estradiol; DSC: Mp. 122.8° C., purity 99.8%; $^1$H-NMR (200 MHz, $CDCl_3$) δ 7.44 (m, 5H), 7.27 (d, 1H, J=8.4 Hz), 6.86 (dd, 1H, $J_1$=2.6 Hz, $J_2$=8.4 Hz), 6.80 (d, 1H, J=2.6 Hz), 6.17 (d, 1H, J=5.8 Hz), 5.78 (dd, 1H, $J_1$=1.4 Hz, $J_2$=3.2 Hz), 5.45 (m, 1H), 5.11 (s, 2H), 2.96 (m, 2H), 2.40-1.54 (m, 10H), 2.18 (s, 3H), 0.93 (s, 3H) ppm.

Example 9 17-Acetyl-3-Benzyl estetrol (compound 3; A=benzyl, C=acetyl)

$OsO_4$ on PVP (9 g, ~5% w/w $OsO_4$ on PVP, prepared according to Cainelli et al. *Synthesis*, 45-47 (1989) was added to a solution of 17-Acetyloxy-3-benzyloxy-estra-1, 3,5 (10),15-tetraene (compound 4; A=benzyl, C=acetyl; 45 g, 112 mmol) in THF (450 mL) and the mixture was heated to 50° C. Trimethylamine-N-oxide dihydrate (24.9 g, 224 mmol) was added portion-wise over 2 h. After stirring for 36 h at 50° C. (TLC showed the reaction to be complete) the reaction mixture was cooled to room temperature. The solids were filtered off, washed with THF (100 mL) and the filtrate was concentrated. The residue was taken up in EtOAc (250 mL) and water (250 mL) was added. The aqueous layer was acidified with 1 N HCl (ca. 10 mL). The layers were separated and the aqueous layer was extracted with EtOAc (150 mL). The organic layers were combined, dried ($Na_2SO_4$) and concentrated in vacuo. The residue was triturated with heptanes/EtOAc (1:1, 100 mL), stirred for 2 h and the resulting white precipitate was filtered off to give the product as a white solid (41 g, 94 mmol, 84%). The product was purified by recrystallization from heptanes/ethyl acetate/EtOH (2:1:1) three times to afford a white solid (21 g, 48.2 mmol, 43%). HPLC-MS: 99.5% βαα-isomer; DSC: Mp. 159.3° C., purity 98.7%; $^1$H-NMR (200 MHz, CDCl$_3$) δ 7.49 (m, 5H), 7.27 (d, 1H, J=8.4 Hz), 6.84 (dd, 1H, J$_1$=2.6 Hz, J$_2$=8.4 Hz), 6.81 (d, 1H, J=2.4 Hz), 5.11 (s, 2H), 4.45 (d, 1H, J=4.4), 4.11 (m, 3H), 3.12 (m, 1H) 2.95 (m, 2H), 2.46-1.64 (m, 10H), 2.24 (s, 3H), 0.93 (s, 3H) ppm.

Example 10 17-Acetyl estetrol (compound 2; C=acetyl)

To a solution of 17-acetyl-3-benzyl estetrol (compound 3; A=benzyl, C=acetyl; 21 g, 48.2 mmol) in MeOH (600 mL, HPLC-grade) was added a preformed suspension of 10% Palladium on activated carbon (2 g) in methanol (50 mL). The mixture was placed under an atmosphere of H$_2$ at 1 atm and stirred for 24 h (TLC showed the reaction to be completed) at room temperature. It was filtered over Celite® and the filter cake was washed with MeOH (200 mL). The filtrate was concentrated in vacuo to give 17-acetyl estetrol as a white solid (15 g, 43.4 mmol, 90%). TLC: R$_f$=0.2 (heptanes/ethyl acetate=1/1); HPLC-MS: 99.2%, DSC: Mp. 212.2° C., purity 98.9%; $^1$H-NMR (200 MHz, CD$_3$OD) δ 7.14 (d, 1H, J=8.0 Hz), 6.60 (dd, 1H, J$_1$=2.6 Hz, J$_2$=8.8 Hz), 6.56 (d, 1H, J=2.4 Hz), 4.81 (dd, 1H, J$_1$=3.4 Hz, J$_2$=6.4 Hz), 4.07 (m, 3H), 3.12 (m, 1H), 2.85 (m, 2H), 2.37-1.37 (m, 10H), 2.18 (s, 3H), 0.91 (s, 3H) ppm.

Example 11 Estetrol

17-Acetyl-estetrol (compound 2; C=acetyl; 15 g, 43.4 mmol) and K$_2$CO$_3$ (6 g, 43.4 mmol) were suspended in MeOH (500 mL, HPLC-grade) and stirred for 4 h at room temperature (TLC showed the reaction to be complete). The solvents were evaporated in vacuo. Water (200 mL) and CHCl$_3$ (70 mL) were added and the mixture was stirred and neutralized with 0.1 N HCl (50 mL). The product was collected by filtration, washed with water (100 mL) and CHCl$_3$ (100 mL) to give estetrol as a white solid (12.2 g, 40.1 mmol, 92.5%, overall yield from estrone 10.8%) after drying at 40° C. in an air-ventilated oven. TLC: R$_f$=0.05 (heptanes/ethyl acetate=1/1); HPLC-MS: 99.1%, DSC: Mp. 243.7° C., purity 99.5%; $^1$H-NMR (200 MHz, CD$_3$OD) δ 7.14 (d, 1H, J=8.6 Hz), 6.61 (dd, 1H, J$_1$=2.6 Hz, J$_2$=8.4 Hz), 6.56 (d, 1H, J=2.4 Hz), 4.83 (m, 1H), 3.93 (m, 3H), 3.50 (d, 1H, J=5.2), 3.38 (m, 2H), 2.84 (m, 2H), 2.32 (m, 3H), 1.97 (m, 1H), 1.68-1.24 (m, 5H), 0.86 (s, 3H) ppm.

The invention claimed is:

1. A process for the preparation of estra-1,3,5(10)-trien-3,15α,16α,17β-tetraol, comprising:
  (a) converting estrone into 3-A-oxy-estra-1,3,5(10),15-tetraen-17-one, wherein A is a protecting group;
  (b) reducing the 17-keto group of 3-A-oxy-estra-1,3,5(10),15-tetraen-17-one to 3-A-oxy-estra-1,3,5(10),15-tetraen-17β-ol;
  (c) protecting the 17-OH group of 3-A-oxy-estra-1,3,5(10),15-tetraen-17β-ol to 3-A-oxy-17-Cp-oxy-estra-1,3,5(10),15-tetraene, wherein Cp is a protecting group;
  (d) oxidizing the carbon-carbon double bond of ring D of 3-A-oxy-17-Cp-oxy-estra-1,3,5(10), 15-tetraene to protected estetrol; and
  (e) removing the protecting groups;
  wherein the protecting group A is selected from an C$_1$-C$_5$ alkyl group or a C$_7$-C$_{12}$ benzylic group and the protecting group Cp is selected from the group consisting of C$_1$-C$_5$ carboxylates.

2. The process according to claim 1, wherein the protecting group A is a C$_7$-C$_{12}$ benzylic group.

3. The process according to claim 1, wherein the the protecting group Cp is acetyl.

4. The process according to claim 1, wherein the reduction of the carbonyl group is carried out using a reducing agent selected from the group of metal hydride compounds.

5. The process according to claim 4, wherein the metal hydride compound is selected from the group consisting of LiAlH$_4$, NaBH$_4$, NaBH(OAc)$_3$, ZnBH$_4$, and NaBH$_4$/CeCl$_3$.

6. The process according to claim 5, wherein the metal hydride compound is NaBH$_4$ in combination with CeCl$_3$ hydrate.

7. The process according to claim 1, wherein the oxidation of the carbon-carbon double bond in ring D is carried out with an oxidizing agent comprising osmium tetroxide.

8. The process according to claim 7, wherein the oxidizing agent is osmium tetroxide immobilized on poly-4-vinylpyridine.

9. The process according to claim 1, wherein the oxidation of the carbon-carbon double bond in ring D is carried out with a catalytic amount of osmium tetroxide immobilized on poly-4-vinylpyridine.

10. The process according to claim 9, wherein the osmium tetroxide immobilized on poly-4-vinylpyridine is used in combination with a co-oxidant.

11. The process according to claim 10, wherein the co-oxidant is selected from the group consisting of trimethylamine-N-oxide, N-methyl morpholine-N-oxide or hydrogen peroxide.

12. The process according to claim 11, wherein the co-oxidant is trimethylamine-N-oxide.

13. The process according to claim 1, wherein the protective C$_7$-C$_{12}$ benzylic group is removed by catalytic hydrogenation conditions.

14. The process according to claim 13, wherein the catalytic hydrogenation conditions comprise a hydrogenation reaction using Pd on activated carbon under a hydrogen atmosphere.

15. The process according to claim 1, wherein the protective C$_1$-C$_5$ alkyl group is removed by using BBr$_3$.

16. The process according to claim 1, wherein protecting group A is removed first to form 17-OCp protected estetrol and subsequently protecting group Cp is removed to form estetrol.

17. The process according to claim 2, wherein the C$_7$-C$_{12}$ benzylic group is a benzyl group.

* * * * *